United States Patent [19]

Nissen et al.

[11] 4,288,636

[45] Sep. 8, 1981

[54] PREPARATION OF CITRAL

[75] Inventors: Axel Nissen, Leimen; Walter Rebafka, Eppelheim; Werner Aquila, Mannheim, all of Fed. Rep. of Germany

[73] Assignee: BASF Aktiengesellschaft, Fed. Rep. of Germany

[21] Appl. No.: 158,346

[22] Filed: Jun. 10, 1980

[30] Foreign Application Priority Data

Jun. 30, 1979 [DE] Fed. Rep. of Germany ....... 2926562

[51] Int. Cl.³ .................. C07C 45/51; C07C 47/21
[52] U.S. Cl. ................................................. 568/486
[58] Field of Search ........................................ 568/486

[56] References Cited

U.S. PATENT DOCUMENTS

| | | | |
|---|---|---|---|
| 2,501,144 | 3/1950 | Saunders | 568/486 |
| 2,987,551 | 6/1961 | Baxter et al. | 568/486 |
| 3,928,459 | 12/1975 | Mercier | 568/486 |
| 3,978,092 | 8/1976 | Ichikawa et al. | 568/486 |
| 4,016,212 | 8/1977 | Leimgruber et al. | 568/486 |
| 4,123,464 | 10/1978 | Leimgruber et al. | 568/486 |
| 4,209,644 | 1/1980 | Ichikawa et al. | 568/468 |

FOREIGN PATENT DOCUMENTS 2411530 9/1974 Fed. Rep. of Germany ...... 568/486

Primary Examiner—Werren B. Lone
Attorney, Agent, or Firm—Keil & Witherspoon

[57] ABSTRACT

Citral (I)

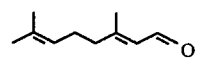

is prepared by heating an acetal (IIa) or (IIb)

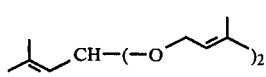

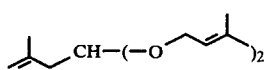

in the presence of an acid catalyst while continuously distilling from the reaction mixture the 3-methylbut-2-en-1-ol (III, prenol) eliminated during the reaction.

4 Claims, No Drawings

PREPARATION OF CITRAL

The present invention relates to an improved process for the preparation of citral (I; 3,7-dimethylocta-2,6-dien-1-al)

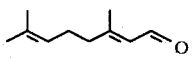  I by heating an acetal of the general formula IIa or IIb

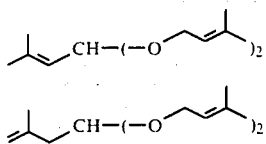

in the presence of an acid catalyst.

Apart from the improvement according to the invention, the essential features of this reaction are disclosed in German Laid-Open Application DOS 2,411,530. It is a complex reaction involving three stages, as shown by the equations below.

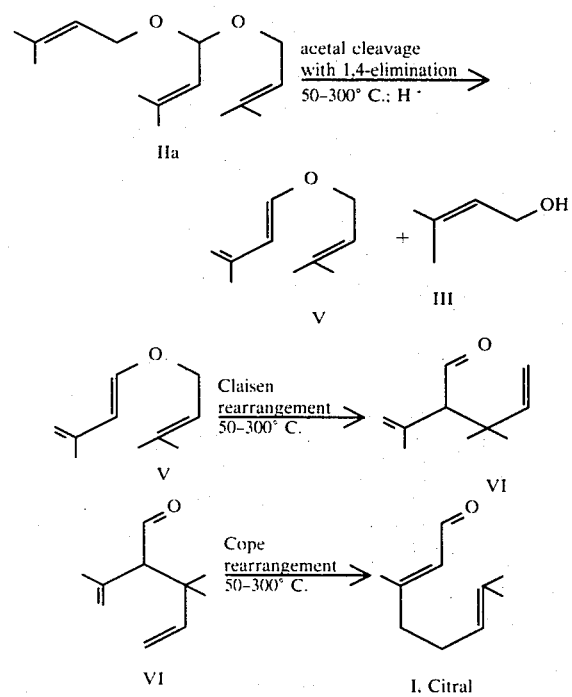

The reaction takes place similarly if instead of the acetals IIa the isomeric acetals IIb are employed.

Since the starting compounds IIa and IIb, the product I, and the by-products and intermediates III, V and VI are sensitive substances, which can react in undesired ways, the yields of I hitherto achievable were only 60–70%.

It is an object of the present invention to improve the yield of I, ie. the important fragrance material citral, and hence to make the process more economical overall.

We have found that this object is achieved and that citral (I)

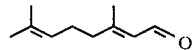  I is obtained in high yields by heating an acetal of the general formula IIa or IIb

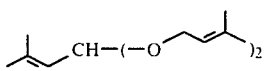  IIa in the presence of an acid catalyst if the 3-methylbut-2-en-1-ol (III, prenol) eliminated in this reaction is continuously removed from the reaction mixture.

Further, we have found that particularly good results are achieved if the reaction is carried out in the presence of from 0.1 to 10 mole%, based on IIa or IIb employed, of an inert liquid IV which under the reaction pressure boils at a higher temperature than prenol but at a lower temperature than citral, 2,8-dimethyl-5-oxa-nona-1,3,7-triene (V) and 2,4,4-trimethyl-3-formylhexa-1,5-diene (VI). These liquids IV are hereafter referred to as intermediate-boiling liquids.

Continuous removal of prenol, in accordance with the invention, increases the yield of citral to about 85–90%. This effect must be described as surprising since the preparation of I is not an equilibrium reaction which could be favored by removal of the prenol from the equilibrium. Furthermore, it is particularly surprising that the yield of citral can be increased to as much as 95% by the presence of the intermediate-boiling liquid IV. The mode of action of the latter, which according to its definition boils at a higher temperature than prenol (boiling point 140° C. under atmospheric pressure, cf. below) but at a lower temperature than citral (boiling point 210° C.) and than the intermediates V (boiling point 205° C.) and VI (boiling point 200° C.) is presumably attributable to the fact that because of the relative partial pressures citral, V and VI remain predominantly in the liquid phase and that the partial pressure of prenol is reduced, as a result of which the latter can rapidly and almost completely be removed continuously. The mixture of predominantly III and IV which passes into the gas phase is then fractionated so that III is taken off at the top of the fractionating column whilst the intermediate-boiling liquid IV runs back into the reaction mixture or is held in the column.

The reaction is preferably carried out at 100°–160° C. under atmospheric pressure or—which is particularly advisable—under reduced pressure, namely 40–140 mbar, measured at the top of the fractionating column. Accordingly, when operating under atmospheric pressure an intermediate-boiling liquid which boils at 140°–°190° C. should be used, eg. diisoamyl ether (boiling point 172° C.), anisole (boiling point 155° C.) and pseudocumene (boiling point 169° C.). If the process is carried out under reduced pressure, the relations of the boiling points of the important substances as a rule remain the same, so that, for example, the above liquids can also be used under these conditions. Particularly suitable intermediate-boiling liquids are the ethers IVa and IVb

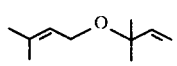  IVa, 3,3,7-trimethyl-4-oxa-octa-1,6-diene

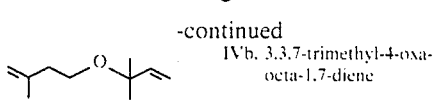
IVb, 3,3,7-trimethyl-4-oxa-octa-1,7-diene which are obtained as by-products when synthesizing II from prenol and 3-methylbut-2-en-1-al.

Since the purpose of using the intermediate-boiling liquids is to facilitate the removal of prenol, but the prenol concentration in the reaction mixture is low because of the measures provided by the invention, the concentration of the intermediate-boiling liquid in the liquid reaction mixture need not be very high. Preferably, the intermediate-boiling liquids IV are therefore employed in amounts of 0.1–10 mole%, especially 0.5–5 mole%, based on IIa or IIb employed. During the reaction, the greater part of the intermediate-boiling liquid is not present in the liquid reaction mixture but in the lower zone of the distillation column.

The acetals IIa and IIb from which citral is derived are known and may be obtained in a conventional manner by acetalizing the aldehydes VIIa and VIIb

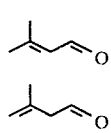

VIIa

VIIb with prenol (III).

The conversion of IIa or IIb to I is carried out in a conventional manner in the presence of an acid catalyst; non-volatile proton acids, eg. sulfuric acid, p-toluenesulfonic acid and especially phosphoric acid have proved particularly suitable catalysts. The amount of the acid depends on its strength and is in general from 0.001 to 0.5% by weight, based on the total amount of the reaction mixture. Where phosphoric acid is used, the preferred concentration range is 0.005–0.05% by weight. It is often advantageous only to add the acid catalyst when a temperature above the boiling point of prenol (III) has been reached. This is especially the case if crude IIa or IIb, containing prenol, is used as the starting material.

It is a particular advantage of the process according to the invention that the presence of a solvent is unnecessary. It is true that the intermediate-boiling liquid IV can be regarded as a solvent, but the required amount thereof is substantially less than the amount of solvent or diluent which would normally be used to suppress undesired side-reactions. If it is nevertheless desired to use a solvent in addition to the intermediate-boiling liquid, it is advisable that this solvent should be higher-boiling than citral, and should, for example, be a high-boiling gasoline fraction.

The amount of solvent is preferably from 0.5 to 3 times the volume of IIa or IIb.

To remove the prenol by distillation and at the same time retain the higher-boiling components of the reaction mixture, a fractionating column, advantageously with 10–30 theoretical plates, is used.

Since the intermediates, as well as citral, are very sensitive to oxygen and polymerize easily, it is advantageous to carry out the process with careful exclusion of oxygen and under a protective gas blanket, for example nitrogen. It is furthermore advantageous to carry out the reaction in the presence of $10^{-3}$–10% by weight, based on acetal IIa or IIb employed, of a polymerization inhibitor, preferably a phenolic inhibitor. Examples of the latter are hydroquinone, pyrocatechol, trimethylhydroquinone, 2,6-di-tert.-butyl-p-cresol and tocopherol. To prevent polymerizations in the fractionating column, the inhibitor is advantageously introduced into the reflux at the top of the column.

EXAMPLE 1

A mixture of 2000 g of 98% strength by weight pure 3-methylbut-2-en-al-diprenylacetal (IIa), (the remainder being prenol III, ie. 3-methylbut-2-en-1-ol), 50 g of 3,3,7-trimethyl-4-oxa-octa-1,6-diene (to serve as the intermediate-boiling liquid IVa), 0.5 g of 65% strength by weight phosphoric acid and 2 g of hydroquinone was heated at 145° C. under a nitrogen atmosphere, whilst the prenol eliminated was continuously distilled off through a fractionating column with 15 theoretical plates, under conditions such that the intermediate-boiling liquid was held in the distillation column. The pressure at the top of the column was 90 mbar, and the temperature 80°–83° C. After 6 hours, the reaction was complete, as shown by the fact that the theoretical amount of prenol had been eliminated and hence been virtually quantitatively recovered.

Conventional working up by distillation gave citral in a yield of 96.6%.

Under the same conditions except for using di-tert.-butyl-p-cresol as the inhibitor, a yield of 95.3% was achieved.

Without use of the intermediate-boiling liquid the yield of citral was 89.4%, and without the intermediate-boiling liquid and without inhibitor it fell to 83.8%.

Under the conditions mentioned in the first paragraph of the present Example, ie. using the intermediate-boiling liquid and the inhibitor, but working under atmospheric pressure and hence without continuous removal of prenol, the yield of citral was only 52.2%.

EXAMPLE 2

Using the conditions described in the first paragraph of Example 1, but starting from 3-methyl-but-3-en-1-aldiprenylacetal (IIb), citral was obtained in a yield of 72%.

We claim:

1. In a process for the preparation of citral (I)

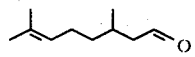

by heating an acetal of the formula IIa or IIb

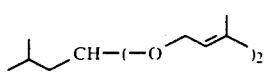

IIa

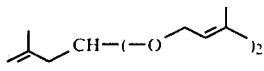

IIb in the presence of an acid catalyst, the improvement which comprises carrying out the reaction at 100°–160° C. in the presence of 0.1–10 mole%, based on IIa or IIb, of an inert liquid IV, which under the reaction pressure boils at a higher temperature than 3-methyl-but-2-en-1-ol (III, prenol) but at a lower temperature than citral, 2,8-dimethyl-5-oxa-nona-1,3,7-triene (V) and 2,4,4-trimethyl-3-formyl-hexa-1,5-diene (VI) while continuously distilling off the prenol eleminated in the reaction over a fractioning column, at the top of which a pressure of 40–140 mbar is maintained.

2. The process of claim 1, wherein the liquid IV is an ether of the general formula IVa or IVb

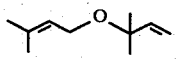 IVa

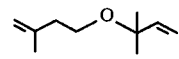 IVb

3. The process of claim 1, wherein the reaction is carried out with exclusion of oxygen.

4. The process of claim 3, wherein the reaction is carried out in the presence of a phenolic polymerization inhibitor.

* * * * *